Figure 1:
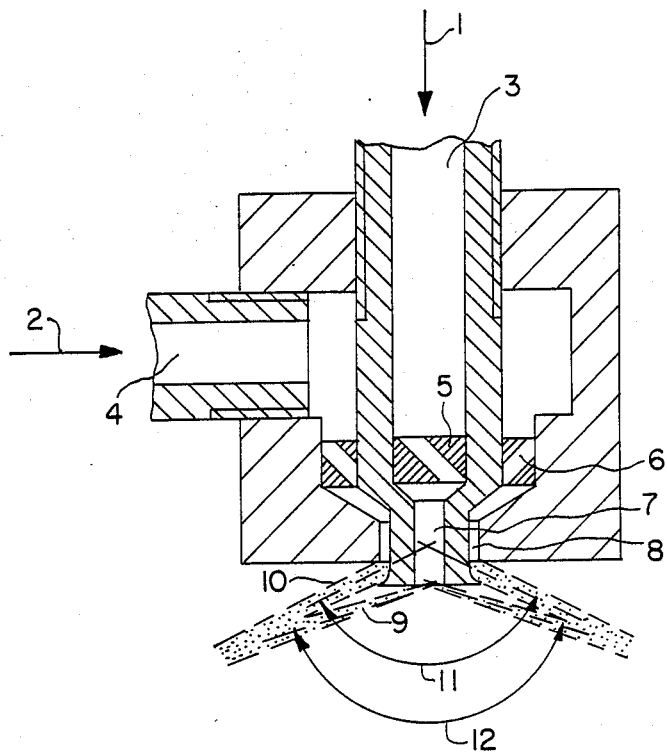

United States Patent [19]

Busse et al.

[11] Patent Number: 4,788,011

[45] Date of Patent: Nov. 29, 1988

[54] PROCESS FOR THE PREPARATION OF CHEMICAL COMPOUNDS OBTAINED AS SOLIDS FROM LIQUID STARTING SUBSTANCES

[75] Inventors: Roland Busse, Leverkusen; Herbert Emde, Cologne; Friedrich Dürholz, Remscheid; Dietmar Mayer, Bergisch Gladbach; Dorde Jovcic, Leichlingen, all of Fed. Rep. of Germany

[73] Assignee: Bayer Aktiengesellschaft, Leverkusen, Fed. Rep. of Germany

[21] Appl. No.: 880,623

[22] Filed: Jul. 1, 1986

Related U.S. Application Data

[63] Continuation of Ser. No. 643,900, Aug. 23, 1984, abandoned.

[30] Foreign Application Priority Data

Aug. 24, 1983 [DE]  Fed. Rep. of Germany ....... 3330445

[51] Int. Cl.$^4$ ................. C07C 143/52; C07C 143/56; C07C 143/24
[52] U.S. Cl. ................. 260/507 R; 260/508; 260/505 N
[58] Field of Search .............. 260/507 R, 508, 505 N; 252/373; 239/404

[56] References Cited

U.S. PATENT DOCUMENTS 3,945,574  3/1976  Polnauer .............................. 239/404
4,420,635  12/1983  Washington et al. ............... 562/555

*Primary Examiner*—Nicky Chan
*Attorney, Agent, or Firm*—Sprung Horn Kramer & Woods

[57] ABSTRACT

Reactions of liquid starting substances to give chemical compounds in which these chemical compounds are obtained as solids can be carried out by spraying the liquid starting substances from separate nozzles such that the liquid starting substances are mixed in the spray cones, which penetrate one another, and thereby react.

13 Claims, 1 Drawing Sheet

PROCESS FOR THE PREPARATION OF CHEMICAL COMPOUNDS OBTAINED AS SOLIDS FROM LIQUID STARTING SUBSTANCES

This is a continuation of application Ser. No 643,900, filed 8/23/84, now abandoned.

The present invention relates to a process for the preparation of chemical compounds from liquid starting substances in which the chemical compound is obtained as a solid.

Mixing liquid starting substances, inter alia for the purpose of reacting these substances to give chemical compounds, is a well-known fundamental operation in chemical technology. This mixing of liquid starting substances can be carried out without problems as long as no substantial changes in the state of aggregation result. In contrast, if the state of aggregation changes very greatly during mixing and reaction of liquid starting substances, in particular as a result of the formation of solids, serious problems arise through encrustation, caking and blockage of reactors and/or fittings, and these require frequent interruption of the process or, in many cases, make processes impossible by this route.

Examples of such reactions are the formation of salts from melts of organic acids, such as organic sulphonic acids, and liquid or liquefied alkalis, such as liquid alkali metal hydroxides, which may contain water, or liquid or liquefied amines. The salts, which are insoluble or inadequately soluble in the liquid starting substances mentioned, of the organic acids mentioned are formed here in an almost instantaneous reaction. These salts then lead to the caking or blockage described, so that further transportation of the liquid starting substances is prevented or at least greatly hindered. However, other reactions of liquid starting substances in which the chemical compounds formed are obtained as solids also suffer from the same difficulties.

In the preparation of alkali metal salts of aromatic hydroxy compounds, it is thus necessary first to react the molten aromatic sulphonic acid on which the product is based with liquid aqueous alkali metal hydroxide solution. According to DE-OS (German Published Specification) No. 1,493,663, this is effected in a tubular mixing chamber into which the two liquid starting substances are introduced tangentially. To avoid caking, there is a multi-edged shaft in this mixing chamber, so that a gap is formed in which the thorough mixing takes place and in which, furthermore, caked material is continuously removed by the uninterrupted rotary motion of this shaft. Not only is such a device troublesome and expensive, since it has to be made of massive material and requires powerful driving forces, but, moreover, rinsing operations must be introduced during breakdowns and when such mechanical mixing devices are removed, since melting of residual caking is frequently no longer possible.

Other mechanical devices for the preparation of alkali metal salts of aromatic hydroxy compounds are, according to British Pat. No. 939,570, a hammer mill or chamber reactors connected in series (DE-OS (German Published Specification) No. 2,813,570).

The apparatus described in British Pat. No. 1,122,078 for the preparation of alkali metal salts of aromatic hydroxy compounds consists of an atomizer disc and mechanical elements for keeping the walls of the kettle below the spraying device free.

A process has now been found for the preparation of chemical compounds obtained as solids from liquid starting substances, which is characterized in that the liquid starting substances are sprayed from separate nozzles such that the liquid starting substances are mixed in the spray cones, which penetrate one another, and thereby react.

The process according to the invention is suitable for thorough mixing and reaction of in principle any desired number of liquid starting substances to form chemical compounds obtained as a solid. In general, however, only two or three liquid starting substances are used. In systems in which more than two liquid starting substances react to form a chemical compound obtained as a solid, it will in many cases also be possible to combine, by premixing to give a liquid phase, two or more of the liquid starting substances which do not yet react with one another to form a chemical compound obtained as a solid, and only then to mix and react the liquid phase with another liquid starting substance, which leads to the formation of the chemical compound obtained as a solid, in the manner according to the invention.

As a result of mixing and reaction of the liquid starting substances in the spray cones which penetrate one another from the separate nozzles, encrustation and blockage of these nozzles is avoided. Furthermore, the chemical compound obtained as a solid is in the form of fine solid particles which, for example, can be collected in a suspending agent in a kettle below the nozzles and thereby give a suspension which is easily stirrable. Thus, if the distance between the nozzles and the surface of the suspending agent mentioned as well as the spatial extent of the spray cones are chosen in a suitable manner, impingement of the solid particles onto the vertical walls of the kettle below the nozzles can be as good as completely avoided, so that caking on the walls and the rinsing operations which correspondingly become necessary can also be avoided entirely.

Neither moving nor static mixing devices are required for the actual mixing and reaction operation.

The nozzles used are known to the expert and the most usual nozzle geometries known at present (slit nozzle, circular nozzle and the like) can be employed.

According to the invention, the arrangement of the nozzles relative to one another is chosen such that the spray cones of the individual nozzles penetrate one another, preferably as far as possible, without the spray cone of one nozzle impinging on the other nozzles. It is thus conceivable that two or more nozzles are arranged obliquely to one another so that the axes of their discharge openings meet at a point outside the nozzles. The discharge direction of the liquid starting substances is thereby preferably chosen sloping downwards. If, for example, three liquid starting substances are used for one reaction, three such nozzles are arranged in a circle. However, it is also possible to arrange a larger number of nozzles in a circle such that the same liquid starting substances flows through every second or every third of the nozzles thus arranged. It is furthermore possible, for example in an elongated horizontal vessel, for two nozzles with a horizontal discharge direction to be arranged opposite one another such that the spray cones meet in the middle between the two nozzles, in which case the reaction product does not fall back on to the nozzle openings but falls between the nozzle openings through to the bottom of the horizontal container, where there is optionally a suspending liquid to collect the small solid particles.

In a preferred embodiment, for example, a concentric two-component nozzle can be used for mixing two liquid starting substances. In the case of this concentric two-component nozzle, one of the two liquid starting substances is discharged through an annular gap and thereby forms a spray cone. The second liquid starting substance is sprayed from a nozzle which issues from the centre of this annular gap and is projected somewhat, so that a second spray cone is formed within the first spray cone. Each of the two spray cones have no contact wth the discharge surface of the other particular spray cone. The inner spray cone has a larger angle than the outer spray cone. In the penetration region (mixing region), the two spray cones form a resultant spray cone, before the spray cones impinge on the surface of a suspending or diluting liquid.

Mixing and reaction of the two liquid starting substances to give the chemical compound obtained in fine solid particles starts at the site where the two spray cones penetrate.

This concentric two-component nozzle can also be extended to a concentric three-component or even multi-component nozzle by locating a second or further annular gap outside the annular gap described above, in which case each additional annular gap located further outside must be constructed behind the inner gap, so that the spray cones which form can penetrate in the gas space below the multi-component nozzle without coming into contact with the nozzle discharge surface of the particular other liquid starting substance.

The feed tube to the nozzle and/or the nozzle discharge opening is preferably designed, in a manner which is known to the expert, such that the cone of liquid starting substance experiences tangential movement along the external surface of the cone in addition to the movement progressing in the axial direction. The individual droplets of the liquid starting substance sprayed in the form of a cone thus describe a spiral line on the surface of the cone, which also widens according to the widening of the cone itself. Particularly preferably, a different spiral thread, in general in the opposite direction, is produced for the different nozzles or, in the case of a concentric two-component or multi-component nozzle, for the individual spray cones. The tangential movements described above on the cone surfaces thereby proceed in the opposite direction for the various spray cones, so that an even more intensive thorough mixing of the liquid starting substances is achieved in the penetration region of the spray cones.

By the detailed geometry of the nozzle known to to the expert, a cone angle (solid angle, this the angle between the centrelines of the individual spray cones) of close to 0° to close to 180° can be formed. A cone angle of close to tube for the liquid starting substance without particular deviation. An angle of close to 180° is approximately comparable to a very flat, completely opened umbrella. The two limit values are not very appropriate for carrying out the process according to the invention. Rather, it is appropriate to establish a cone angle, in the context of the given explanation of this cone angle, of, for example, 10° to 120°, preferably 15° to 90° and particularly preferably 20° to 60°. It is not necessary to establish the same cone angle for the various nozzles. In the particular case of a concentric multi-component nozzle, it is even necessary to provide the inner spray cone with a larger angle than the outer spray cone, which comes from further above, in order to achieve thorough mixing. In such a case, for example, the angle of the inner spray cone is 1° to 40°, preferably 15° to 30°, greater than the angle of the outer spray cone. The angles mentioned relate to the spray cones at the discharge point of the nozzle. A resultant spray cone then forms, starting from the penetration zone of several spray cones, in the manner already described above. The angle of this resultant spray cone is between the various angles of the original spray cones. This applies in particular in the case of the concentric multi-component nozzle described. The geometry of the resultant cone is furthermore determined by the gravitational pull on the solid particles formed and their path influenced by the gravitational pull. The construction of a two-component nozzle is illustrated, by way of example, in FIG. 1. Components 1 and 2 are introduced into nozzles 3 and 4 respectively, and passed through the torsion-imparted elements 5 and 6 respectively, to the nozzle outlets 7 and 8 respectively. Spray cones 9 and 10 are formed. The cones form the solid angles 11 and 12.

The spray cone is formed, in a manner which is known to the expert, such that the pressure within the jet of liquid supplied is greater than that in the space into which this jet is discharged through the nozzle opening. The spray cone consisting of very fine droplets of liquid then forms as a function of this pressure difference and furthermore of the viscosity of the liquid starting substance and of the amount of liquid conveyed per unit time, in connection with the detailed geometry of the nozzle. A greater pressure difference here will produce smaller drops, but will also require a higher consumption of energy to produce this greater pressure difference. A greater pressure difference for a given nozzle geometry will also give rise to a larger angle of the spray cone and will of course also permit a higher throughput per unit time. In contrast, a very small pressure difference will, for example, allow the spray cone to degenerate also to a coherent stream of liquid outside the nozzle. The customary pressure differences for carrying out the process according to the invention are, for example, 0.5 to 50 bar, preferably 0.8 to 30 bar and particularly preferably 1 to 16 bar. Corresponding to the possibility described above of establishing various spray cone angles for the various liquid starting substances, it is also possible to establish these various angles by applying various pressure differences to individual nozzles or nozzle discharge openings.

The absolute pressure is not essential for carrying out the process according to the invention. It can vary from a reduced pressure which can be realized industrially and economically up to very high pressures, for example from 1 mbar to 100 bar. The process according to the invention will frequently be carried out under 0.1 to 80 bar, but a large number of cases of application can be carried out under normal pressure.

The temperature for carrying out the process according to the invention must be between the melting point and the boiling point or decomposition point of the liquid starting substances. Its absolute level depends here on the physical constants of the liquid starting substances and therefore cannot be more closely defined numerically. This temperature furthermore relates to only the feed of the liquid starting substance, the discharge openings of the nozzles and the upper regions of the spray cones for producing liquid droplets. The subsequent setting in the penetration region of the various spray cones and the below is not critical for carrying out the process according to the invention and is in general established by itself. The following boundary conditions apply to this temperature which is established by itself:

(a) The temperature of the liquid starting substances supplied,
(b) the heat of reaction on the basis of the chemical reaction taking place in the penetration zone of the spray cones, for example the neutralization, and
(c) any removal of heat and/or material from the subsequent apparatus.

As examples of the removal of heat or materials mentioned under (c), it may be mentioned that if normal pressure and a temperature greater than 100° C. are established, it is possible to remove, for example, water of neutralization in the form of steam from the reaction space following mixing. A suspension formed from the chemical compound obtained as a solid is thereby concentrated in respect of the amount of water which still remains. As another example, there may be mentioned that if a relatively high pressure is maintained and substances and heat energy are retained within the reactor after the mixing zone, the increase in temperature by the heat of neutralization can be used for carrying out a subsequent chemical reaction, for example a rearrangement in the molecule of the chemical compound obtained as a solid.

The penetration zone of the spray cones thus serves as a mixing and reaction zone for the liquid starting substances fed in. The chemical compound hereby obtained in the form of small solid particles then falls downwards in accordance with the gravitational force on these solid particles and is in general collected in a suspending agent, without substantial prior contact with the walls of the apparatus containing the suspending liquid occurring. The suspending agent here can be any suitable liquid which enables, in the desired manner, a stirrable and transportable suspension of the chemical compound obtained in the form of a solid to be achieved. In the case of neutralization of organic acids by alkali metal salt solutions or amines, this can be, for example, water, in which the salts obtained as a solid are insoluble or not completely soluble, and it can furthermore be an excess of one of the liquid components, for example excess molten organic acid or excess liquid alkali metal hydroxide (optionally as a highly concentrated solution) or liquid amine. However, without impairing the inventive idea, it is also possible to use as the suspending agent inert solvents, such as aromatic or aliphatic hydrocarbons or halogenohydrocarbons, or other suspending agents which are inert towards the chemical compound obtained as a solid or towards any liquid starting substances remaining as excess.

The suspension collected can be kept stable and prevented from settling, for example by a stirrer. The apparatus to be installed below the nozzles can accordingly be a stirred container. The suspension can hereby be intermediately stored up to a predetermined maximum level of fill of the stirred container and then further used batchwise, but it can also be removed continuously for further use via an outlet or overflow. Moreover, horizontal containers are conceivable for collection and intermediate storage of a suspension. It is also possible to collect the suspension in a funnel and to remove it via a sludge pump or a screw discharge or similar conveying devices. The container to be installed below the penetration zone of the spray cones can furthermore have an outlet in the side or on the top for substances to be removed in vapour form, for example the steam from the water of neutralization.

In the process according to the invention, liquid starting substances are sprayed through nozzles to give spray cones. Possible liquid starting substances here are pure liquids, melts of pure substances or of substance mixtures, solutions, emulsions, and suspensions, if the particle size thereof allows such a suspension to be sprayed through the nozzle. It is also possible to spray each liquid starting substance through a separate nozzle. However, since mixed melts, solutions, emulsions or suspensions, that is to say multi-component systems, can, as already described, also be sprayed through one nozzle, it is in principle also possible, in the case of more than two liquid starting substances, to mix two or more of these liquid starting substances before spraying if these do not yet react to give a chemical compound obtained as a solid, and then to spray these together as a mixture of several liquid starting substances and to spray the other critical liquid starting substance, which then reacts to give the chemical compound obtained as a solid, in another separate nozzle.

The process according to the invention is outstandingly suitable for the preparation of salts of organic acids, for example carboxylic acids, sulphonic acids or phosphonic acids, with metal ions, for example alkali metal ions, in highly concentrated form. If such salts are to be prepared in highly concentrated form by conventional processes from melts or highly concentrated solutions of the acid and metal ions, the salts formed immediately solidify to a hard mass which block the reactors, such as mixing pipes or stirred vessels, in a very short time and force the reaction to be interrupted. The process according to the invention is also outstandingly suitable for the preparation of salts of optionally substituted aniline and a mineral acid, preferably sulphuric acid. The process is furthermore outstandingly suitable for the preparation of organic acids which are sparingly soluble in water when the readily water-soluble alkali metal salts of such organic acids are reacted with mineral acid. The difficult technological situations mentioned, however, in principle also arise in the case of all other reactions in which the chemical compounds formed are obtained as solids, in which, that is to say, as a result of the high concentration desired for the substance formed, the amount of solvent present is too little to form a homogeneous liquid base. The following individual cases, for example, may be described in more detail for illustration:

To prepare 3-hydroxybenzoic acid, benzoic acid is first sulphonated with sulphuric acid and/or gaseous or liquid $SO_3$ to give 3-sulphobenzoic acid. This 3-sulphobenzoic acid is then converted into its alkali metal salt, for example into its sodium salt, and the salt is fused with excess alkali metal hydroxide, for example sodium hydroxide, to give the sodium salt of 3-hydroxybenzoic acid, the sulphonic acid group being removed. The penetration of this desired alkali metal salt of 3-sulphobenzoic acid, if appropriate as a mixture with the excess alkali metal hydroxide required in the following alkali melt, can now be carried out in a particularly advantageous manner with the process according to the invention without lumps or blockages by the salt formed occurring. This process is carried out, for example, in a stirred kettle with the customary devices for temperature and pressure measurement. Two nozzles for the liquid starting substances to be fed in are installed in the space between the lid of the stirred kettle and the stirrer and above the level of liquid to be expected later. The concentric two-component nozzle described above is preferably used here. In the case where the stirrer is introduced into the kettle from the top in the customary manner, this concentric two-component nozzle is installed eccentrically in the stirred kettle between the stirrer shaft and the wall. The spray angles of the liquid starting substances discharged are adjusted such that essentially no contact with the wall and no contact with the stirrer shaft occurs. A little splashing is not critical, since the salt of 3-sulphobenzoic acid obtained as small solid particles can easily be rinsed off the wall and off the stirrer shaft in this form. In the simplest case, this rinsing off is effected by the splashing of the suspension agitated in the kettle or in the lower region of the kettle by the stirrer splashing around as a result of the rising level of liquid of the suspension formed. A small amount of water, which is not sufficient to form a solution, or a small amount of the solution of the hydroxide used can be employed as the suspending agent. In the simplest and thus preferred case, no suspending agent is introduced separately, but the water of neutralization formed in the course of the neutralization reaction is used for this. Molten 3-sulphobenzoic acid or, preferably, a technical grade sulphonation melt of 3-sulphobenzoic acid is employed as one of the liquid starting substances. Such a technical grade sulphonation melt can have, for example, the following composition: 70 to 95% by weight of 3-sulphobenzoic acid, 2.5 to 7% by weight of 4-sulphobenzoic acid, 0.5 to 1.5% by weight of 2-sulphobenzoic acid, 0.01 to 0.5% by weight of 3,5-disulphobenzoic acid, 0.01 to 1.5% by weight of diphenylsulphone derivatives, 0.01 to 1.5% by weight benzophenone derivatives and about 2.0 to 20% by weight of $SO_3$ (in the form of $SO_3$ and/or $H_2SO_4$).

The other liquid starting substance is 50 to 100% strength by weight alkali metal hydroxide, the remaining 50 to 0% by weight essentially consisting of water. 60 to 90% strength by weight, in particular 65 to 80% strength by weight, alkali metal hydroxide is preferably used. Possible alkali metal hydroxides are, for example, sodium hydroxide and potassium hydroxide, preferably sodium hydroxide.

The temperature range from 20° to 350° C., preferably 90° to 200° C., is suitable for the liquid starting substances.

Since an amount of alkali metal hydroxide greater than that required stoichiometrically for salt formation is mixed with the 3-sulphobenzoic acid or the sulphonation mixture for the alkali fusion following the salt formation, the amount of alkali metal hydroxide is chosen so that, after neutralization of all the sulpho and carboxyl groups and, in the case of the sulphonation melt, also after neutralizatoin of the sulphuric acid, a further 2.5 to 8 mol, preferably 3 to 6 mol, particularly preferably 3.5 to 5.5 mol and especially preferably 4 to 5 mol, of alklai metal hydroxide are still present per mol of 3-sulphobenzoic acid.

The liquid starting substances mentioned are kept liquid in separate stirred containers and are fed via metering pumps to the nozzles, preferably the concentric two-component nozzle, and sprayed into the gas space of the stirred kettle. Preferably, the acid or the acid sulphonation melt is hereby sprayed via the centrally placed projecting nozzle with a larger spray cone angle, whilst the liquid alkali metal hydroxide is sprayed via the externally located annular gap with a smaller spray cone angle than the angle of the inner spray cone. In particular, corrosion of all the components of the apparatus by the acid or the acid sulphonation melt is hereby prevented, since all the acid constituents from the inner spray cone must always first pass through the outer alkaline spray cone before contact with the wall or contact with the stirrer shaft, and are thereby neutralized and rendered harmless.

The salt formation in this reaction can be furthermore steered, by applying an increased pressure in the stirred kettle of, for example, 30 to 80 bar, preferably 40 to 60 bar, such that only a minor amount of the water of neutralization vaporizes and all of the heat of neutralization is thus retained in the suspension of the salt. Heating up of the suspension for the subsequent alkaline melt is thus substantially avoided, so that the entire process can be operated under extremely favourable conditions, taking into account the following stage.

Excess alkali metal hydroxide is used as the suspending agent in this case.

In another example, the preparation of 4,4'-dihydroxy-diphenyl may be referred to, in which diphenyl-4,4'-disulphonic acid is first formed from diphenyl by sulphonation and is converted into the di-alkali metal salt by salt formation and the salt is then converted into the di-alkali metal salt of 4,4'-dihydroxy-diphenyl in the presence of excess alkali metal hydroxide, the sulphonic acid groups being removed.

In a manner similar to that just described for 3-hydroxy-benzoic acid, the molten disulphonic acid or, preferably, a technical grade sulphonation mixture can be used as the starting substance here. Such a technical grade sulphonation mixture can have, for example, the following composition: at least 30% by weight, for example 30 to 80% by weight, of diphenyl-4,4'-disulphonic acid, 0 to 8% by weight of diphenyl-3,4'-disulphonic acid, 0 to 5% by weight of diphenyl-3,3'-disulphonic acid, 0 to 2% by weight of diphenyl-4-sulphonic acid, 0 to 54% by weight of sulphuric acid and 30 to 1% by weight of water.

The alkali metal hydroxide, preferably sodium hydroxide, is also preferably used here in a concentration of at least 50% by weight of alkali metal hydroxide, the remainder essentially being water. A concentration of 50 to 96% by weight, preferably 60 to 95% by weight and particularly 65 to 85% by weight, of alkali metal hydroxide may be mentioned by way of example. The amount of alkali metal hydroxide which should be present in addition to that for neutralization of all the acid groups in the disulphonic acid employed or in the sulphonation mixture employed is 8 to 24 mol of alkali metal hydroxide per mol of diphenyldisulphonic acid, preferably 11 to 17 mol of alkali metal hydroxide.

The temperatures already mentioned are suitable for the starting substances employed. Preferably, the concentric two-component nozzle in which the acid liquid starting substance is sprayed via the central nozzle is also again used here. The pressure in the stirred kettle can also be set at a higher value in this case, to keep the heat of neutralisation in the suspension formed. However, for further concentration of the suspension of the di-alkali metal salt, it is also possible to remove steam from the stirred kettle under normal pressure.

The same procedure can in principle be followed if diphenyl-monosulphonic acid is used as the starting substance for the formation of monohydroxy-diphenyl and the subsequent procedure is via alkali metal salt formation and an alkaline melt.

3-Hydroxybenzoic acid is an important intermediate for the preparation of plant protection agents. Thus, according to U.S. Pat. No. 4,031,131, 3-hydroxy-benzoic acid can be reacted with 3,4-dichlorobenzotrifluoride in methanolic solution and in the presence of potassium hydroxide and dimethylsulphoxide to give 3-(2-chloro-4-trifluoromethylphenoxy)-benzoic acid, which can be further converted, by nitration with potassium nitrate in concentrated sulphuric acid, into 5-(2-chloro-4-trifluoromethyl-phenoxy)-2-nitrobenzoic acid, which, according to U.S. Pat. No. 3,798,276 is an important herbicide.

Dihydroxy-diphenyls are a starting material for high-grade condensation polymers, such as polycarbonates and polyesters, the property of stability at high temperatures being particularly important (DE-OS (German Published Specification) No. 3,031,094). Dihydroxy-diphenyls are furthermore used as an intermediate for pharmaceutical products and as a stabilizer and antioxidants for rubbers, oils and polymers.

4-Hydroxy-diphenyl(p-phenyl-phenol) is used as a chain stopper for adjusting the molecular weights for the polymers mentioned which are obtained from dihydroxydiphenyl, and is furthermore an intermediate for the preparation of lacquer resins, non-ionic emulsifiers and plant protection agents (Ullmanns Enzyklopädie der Technischen Chemie (Ullmann's Encyclopedia of Industrial Chemistry), 4th Edition, Volume 18, page 219).

The following sulphonic acids, which are converted into the corresponding hydroxy compounds, may be mentioned as examples of other applications: naphthalene-1- and 2-sulphonic acid (give $\alpha$- and $\beta$-naphthol), naphthalene-1,5-disulphonic acid (gives azuric acid=1-hydroxynaphthalene-5-sulphonic acid, or azurol=1,5-dihydroxynaphthalene), the 1,3,6-trisulphonic acid of naphthalene (1-OH-9,6-disulphonic acid), benzenedisulphonic acid (resorcinol), benzenesulphonic acid (phenol), toluenesulphonic acid (cresol) and carbazoletetrasulphonic acid (hydroxycarbazoletrisulphonic acid).

Examples of other feed materials are the isomeric naphthalene-di- and -tri-sulphonic acids, aminonaphthalene-mono-, -di- and tri-sulphonic acids and hydroxynaphthalene-mono-, -di- and -tri-sulphonic acids.

The preparation of aminoaryl-sulphonic acids in which the optionally substituted amine hydrogen sulphate is first formed from an optionally substituted aromatic amine and sulphuric acid and the product is converted into the aminoaryl-sulphonic acid by the so-called baking process may be mentioned as another example of successfully carrying out the process according to the invention. One of the liquid starting substances employed here is an aromatic amine which is optionally substituted in the aromatic nucleus and/or on the amino-nitrogen and in which the aromatic nucleus can be an optionally substituted benzene, naphthalene, anthracene, naphthoquinone or anthraquinone skeleton or the skeleton of an aromatic heterocyclic radical and the amino-nitrogen can be mono- or di-substituted by alkyl, aralkyl or aryl, it furthermore being possible for the nitrogen atom to form a nitrogen-heterocyclic radical with the substituent. The aromatic skeleton is preferably the benzene or naphthalene skeleton, particularly preferably the benzene skeleton. The prototype of this reaction is the conversion of unsubstituted aniline into aniline hydrogen sulphate and subsequently into sulphanilic acid.

Sulphuric acid, which can have a water content of up to 30% by weight, is used as the other liquid starting substance. 96 to 100% strength by weight sulphuric acid is preferably used, and 100% strength sulphuric acid (monhydrate) is especially preferred.

Since the melting points of the liquid starting substances mentioned in this example are very low, the temperature of the liquid starting substances fed in can also be lower than in the abovementioned examples. 0° to 100° C., preferably 15° to 80° C., may be mentioned as an example of the temperature range. Since an excess of one of the two starting substances is not required for the subsequent baking process, the molar ratio of the arylamine and the sulphuric acid is in general adjusted to close to the equivalence point, for example to 0.95 to 1.05 mol of sulphuric acid per mol of arylamine, preferably 0.98 to 1.05 mol and particularly close to 1 mol.

If one selects a higher temperature of both the starting substances, for example 120°–180° C. and meters in the two substances into the hot suspension medium layed before, then the neutralisation heat which occurs on mixing can be employed to produce the aminoarylsulphonic acid in one step via the arylamine hydrogen sulphate. The formed suspension can be usually worked up, for example by filtration or by aqueous alkaline extraction.

The abovementioned stirred kettle with an eccentrically installed concentric two-component nozzle can be used as the apparatus. In the context of prevention of corrosion, the inner cone can in this case also be formed by the sulphuric acid, whilst the outer cone is formed from the liquid or molten arylamine or, if appropriate, the arylamine dissolved in a solvent.

Aminoarylsulphonic acids are useful intermediates for the preparation of pharmaceuticals, foams, optical brighteners, wetting agents, synthetic disinfectants, tanning agents, reserve agents, insecticides, finishing agents, plasticizers and polymeric thickeners (Ullmanns Enzyklopädie der Technischen Chemie (Ullmann's Encyclopedia of Industrial Chemistry), 3rd Edition, Volume 16, page 561).

The homogeneity of the initially formed arylammonium hydrogen sulphate which is required for the successful course of the baking process and for achieving a high quality of the aminoarylsulphonic acid is achieved to a particularly high degree in the process according to the invention.

Another example of the application of the process according to the invention is the production of free H-acid (1-amino-8-hydroxynaphthalene-3,6-disulphonic acid) by reaction of the sodium salt with sulphuric acid or another mineral acid. Thus, in the preparation of H-acid from the trisodium salt of 1-aminonaphthalene-3,6,8-trisulphonic acid and hot sodium hydroxide solution, an aqueous solution is obtained which chiefly contains H-acid Na salt, sodium sulphite and excess NaOH and is reacted with sulphuric acid, $SO_2$ being evolved (Ullmanns Encyklopädie der technischen Chemie (Ullmann's Encyclopedia of Industrial Chemistry), 4th Edition, Volume 17, page 104). The aqueous solution and the sulphuric acid are sprayed from separate nozzles in the manner described above, such that their spray cones penetrate, free H-acid being formed as a solid, which is then taken up in the acid solution of the resulting salt as the suspending agent. A concentric two-component nozzle, the spray cones of which have different angles, can again preferably be used here.

The following summary contains the most important advantages of the process according to the invention:

1. No mechanical mixers or mixing devices are necessary; baking of the reaction mixture formed is thereby avoided, so that rinsing devices can be dispensed with.
2. The heat of reaction, for example of a neutralisation reaction, can be utilised either to increase the temperature of the suspension collected or to evaporate out excess water or solvent.
3. The extremely fine division of the mixture in the free space provides a large surface area which results in good preconditions for foam-free removal of water, solvent or volatile secondary components by distillation.
4. The extremely fine division and thorough intimate mixing for the reaction of the liquid starting substances takes place in the free space, which means that corrosion problems from aggressive reaction partners, for example from free acids, are not to be feared.
5. The chemical compound obtained as a solid is formed as small fine solid particles, so that a finely divided, easily stirrable and easily transportable suspension which facilitates all subsequent processing steps is formed.
6. The uniform, simultaneous very finely divided thorough mixing of the reaction partners prevents local overheating.
7. Compared with the known mechanical mixing devices, the process according to the invention has the advantage of small installation dimensions of the nozzles required, and can therefore easily be subsequently incorporated and carried out in existing apparatuses.
8. The heating up time for any subsequent melt reaction can be shortened or dispensed with completely as a result of the possibility of keeping the heat of neutralisation within the suspension formed.
9. In the case of neutralisation and formation of salts of organic acids for the purpose of a subsequent melt reaction, the separate process steps of neutralisation, drying and intermediate storage of the dried salt and its transportation and introduction into the melt reactor are saved or combined.
10. In the case of the preparation of the di-alkali metal salt of diphenyl-disulphonic acid for the purpose of the subsequent alkaline melt for the preparation of dihydroxy-diphenyl, the amount of sodium hydroxide used of 20 mol per mol of disulphonic acid in the process according to the prior art can be reduced to 8–24 mol, preferably to 11–17 mol, in the process according to the invention because of the formation of the very finely divided, easily stirrable suspension.
11. The production of aminoaryl sulphonic acids in a suspension medium can be performed without any thinkable baking-on as well as without any chemical reaction of one of the starting substances with the suspension medium.

EXAMPLE 1

A 20 liter stirred autoclave with a stirrer inserted centrally from the top and an eccentrically located concentric two-component nozzle was utilised as the reaction apparatus. 8.5 kg of a technical grade sulphonation mixture containing 84% by weight of 3-sulphobenzoic acid with a temperature of 100° C. under a pressure of 40–60 bar and 14.2 kg of 74% strength aqueous sodium hydroxide solution with a temperature of 100° C. under a pressure of 40–60 bar were simultaneously sprayed through this two-component nozzle in the course of 15 minutes, the acid being sprayed via the inner nozzle and the alkali via the outer annular gap. A pressure of 30–50 bar and a temperature of 320°–330° C. were established in the stirred kettle. The water of neutralisation and the excess sodium hydroxide solution formed the suspending agent, the surface of which rose within the stirred kettle in the course of the experiment. The inner spray cone had an angle of about 60°, and the outer spray cone had an angle of 30°, so that a resultant angle of about 45° was established, starting from the penetration zone. The spray height from the nozzle to the surface of the suspension was initially 55 cm, and was 12 cm at the end of the experiment.

EXAMPLE 2

44.3 kg/hour of diphenyldisulphonic acid melt containing 65.6% by weight of diphenyl-4,4'-disulphonic acid with a temperature of 100° C. under a pressure of 4 bar and 44.3 kg/hour of 74% strength by weight aqueous sodium hydroxide solution with a temperature of 100° C. and a pressure of 4 bar were sprayed, in a 100 liter stirred kettle with a diameter of 600 mm, which was equipped analogously to that in Example 1, through a concentric two-component nozzle into the stirred kettle, which was kept under a pressure of 1 bar, the acid melt being fed through the inner nozzle and the sodium hydroxide solution being fed through the outer annular gap. The water which vaporised was condensed and fed back into the kettle. A temperature of 145°–147° C. was established in the kettle. The spray height was initially about 55 cm and at the end was about 25 cm. If the condensate does not run back into the kettle, a kettle temperature of 165° C.–170° C. is established.

EXAMPLE 3

40 kg/hour of an approximately 30% strength by weight aqueous solution of H-acid trisodium salt, NaOH and $Na_2SO_3$ and 13 kg/hour of approximately 60% strength $H_2SO_4$ were simultaneously sprayed into an apparatus as in Example 2 (spray angle: 45° external, 75° internal); the $H_2SO_4$ was passed through the inner nozzle. The temperature of the substance streams, which were sprayed in at about 40°–80° C., rose to about 100° C. in the suspension, as a result of the heat of neutralisation, the $SO_2$ formed being at the same time completely gassed out. The suspension of H-acid in the acid solution formed in the bottom of the kettle could be removed from the kettle without difficulty at the rate at which it was formed, and fed for further working up.

What is claimed is:

1. In a process for the preparation of solid salts of organic sulphonic acids by contacting a first reactant in liquid phase with a second reactant in liquid phase, the improvement wherein said first reactant is formed into a first spray cone in the form of a spiral thread, said second reactant is formed into a second spray cone in the form of a sprial thread said first spray cone is caused to penetrate said second spray cone and said second spray cone is caused to penetrate said first spray cone wherein said first spray cone in the form of a spiral thread and said second spray cone in the form of a spiral thread emanate in opposite directions from one another.

2. A process according to claim 1 wherein said spray cones are formed in a concentric two-component nozzle comrpising a first nozzle component which forms a spray defining an annular gap and a nozzle component therein which directs a spray into said annular gap.

3. A process according to claim 1 wherein the angle of the spray cone is 5 to 120 degrees.

4. A process according to claim 2 wherein the spray directed into said annular gap has an angle of 1 to 40 degrees greater than that of the outer spray cone.

5. A process according to claim 1 wherein said first reactant is a molten aromatic sulfonic acid and said second reactant is a liquid alkali metal hydroxide, said reactants are separately passed through nozzles to form spray cones which penetrate one another and thereafter the resultant reaction mixture is mixed and neutralization is effected downstream of said nozzles.

6. A process according to claim 5 wherein a technical grade sulfonation mixture containing at least 30 percent by weight of diphenyl-4,4'-disulfonic acid is employed as said aromatic sulfonic acid and said alkali metal hydroxide is sodium hydroxide in a concentration of at least 50 percent by weight in an aqueous solution, said sodium hydroxide is employed in an amount such that, following neutralization of said disulfonic acid there are 8 to 24 mols per mol of a diphenyl-4,4'-disulfonic acid sodium salt in the resultant reaction mixture.

7. A process according to claim 1 wherein said first reactant is an arylamine in pure liquid form or dissolved in a solvent said second reactant comprises sulfuric acid, said first reactant is passed through a nozzle to form a first spray cone, said second reactant is passed through a nozzle to form a second spray cone, neutralization of the resultant reaction mixture is effected downstream of said nozzles, the reaction of said first reactant with said second reactant is effected at 120 to 180 degrees C. in one strip to form an aminoaryl sulfonic acid.

8. A process according to claim 7 wherein said sulfuric acid is in admixture with water.

9. A process according to claim 7 wherein said arylamine is an amine of an optionally substituted benzene, naphthalene, anthracene, naphthoquinone or anthraquinone skeleton or the skeleton of an aromatic heterocyclic radial and the amino nitrogen can be mono- or di-substituted by alkyl, aralkyl or aryl, it furthermore being possible for the nitrogen atoms to form a nitrogen-heterocyclic radical with the substituent.

10. A process according to claim 9 wherein said sulfuric acid has a water content and such water content is up to 30 weight percent based on the combined weight of water and sulfuric acid.

11. A process according to claim 7 wherein said spray cones are formed employing a concentric two-component nozzle and the acid component is sprayed from a centrally disposed nozzle into an annular gap disposed by the spray cone formed by a spray nozzle disposed about said centrally disposed nozzle.

12. A process according to claim 5 wherein said spray cones are formed employing a concentric two-component nozzle and the acid component is sprayed from a centrally disposed nozzle into an annular gap disposed by the spray cone formed by a spray nozzle disposed about said centrally disposed nozzle.

13. A process according to claim 5 wherein said aromatic sulfonic is 3-sulfobenzoic acid.

* * * * *